United States Patent [19]

Hammond et al.

[11] Patent Number: 5,386,009
[45] Date of Patent: Jan. 31, 1995

[54] LIPOPEPTIDE DERIVATIVES

[75] Inventors: Milton L. Hammond, Somerville; Robert E. Schwartz, Westfield; James M. Balkovec, North Plainfield, all of N.J.

[73] Assignee: Merck & Co. Inc., Rahway, N.J.

[21] Appl. No.: 495,200

[22] Filed: Mar. 19, 1990

[51] Int. Cl.[6] ................... A61K 37/02; C07K 5/12; C07K 7/06
[52] U.S. Cl. .................................................... 530/317
[58] Field of Search ..................... 530/371; 514/11

[56] References Cited

U.S. PATENT DOCUMENTS

| | | | |
|---|---|---|---|
| 4,288,549 | 9/1981 | Breck et al. | 435/119 |
| 4,293,490 | 10/1981 | Abbott et al. | 530/317 |
| 4,293,491 | 10/1981 | Debono et al. | 530/317 |
| 4,320,054 | 3/1982 | Abbott et al. | 530/317 |
| 4,322,338 | 3/1982 | Abbott et al. | 530/317 |
| 4,791,100 | 12/1988 | Kramer et al. | 514/612 |
| 4,931,352 | 6/1990 | Fromtling et al. | 530/317 |

FOREIGN PATENT DOCUMENTS

0431350A1 6/1991 European Pat. Off. .
0462531A1 12/1991 European Pat. Off. .

OTHER PUBLICATIONS

Traver et al., Helv. Chim. Acta 62, 4, 1252-67 (1979).
Pache, W. et al., 13th International Congress Chemotherapy (1983), PS 4.8/3, Part 115, Abstract No. 10; also references in Ann. Reports in Med. Chem. 19, Sec. III, 130–131.

*Primary Examiner*—Robert J. Hill, Jr.
*Assistant Examiner*—S. G. Marshall
*Attorney, Agent, or Firm*—Elliott Korsen; Mark R. Daniel; Joseph F. DiPrima

[57] ABSTRACT

The present invention is directed to water-soluble derivatives of antibiotic lipopeptides. The derivatives have good solubility properties in aqueous medium, rendering them more useful as therapeutic agents.

7 Claims, No Drawings

LIPOPEPTIDE DERIVATIVES

The present invention is directed to a compound having the formula

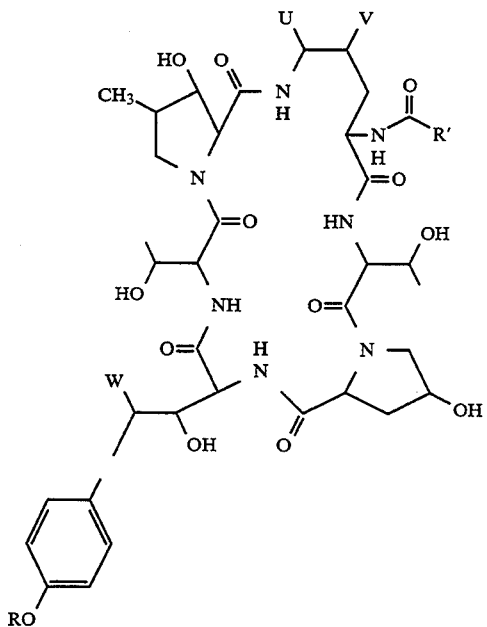

(A)

In this and succeeding formulas, R is an acyl, phosphono or sulfo radical which possesses a charged group at neutral pH; R' is a $C_5$-$C_{23}$ alkyl, $C_5$-$C_{23}$ alkenyl, $C_5$-$C_{23}$ alkynyl or aryl; U, V and W are independently H or OH. In the preferred compounds (1) U, V and W are all OH; (2) U and W are H and V is OH; and (3) U is H and V and W are OH.

The alkyl, alkenyl and alkynyl groups may be either straight chain or branched. When alkenyl or alkynyl, from 1 to 3 unsaturated groups may be present. Especially preferred are $C_{13}$ to $C_{17}$ groups such as tridecyl, pentadecyl, 8,11-heptadecadienyl, 7-pentadecenyl, 10-heptadecenyl, 9,11-dimethyltridecyl, and the like.

By the expression "aryl" is meant preferably phenyl or substituted phenyl. Substituents may be alkyl, alkyloxy, alkylthio, alkylamino. The carbon content of the alkyl is from 1 to 10. The preferred substituted aryl may be represented by

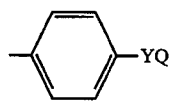

wherein Y is $CH_2$, S, O or NH and Q is $C_{6-10}$alkyl. A preferred member of this group is a radical in which Y is O, and Q is $C_8H_{17}$.

"Acyl, phosphono or sulfo radicals which possess a charged group at neutral pH" include those which may be an anion from an acid or a cation form of an amine base and may be further defined as follows:

(1) $PO_3AH$ wherein A is H, $C_1$-$C_6$ alkyl, phenyl or substituted phenyl in which the substituent is alkyl, alkyloxy, alkylthio, or alkylamino, or a cation salt thereof;

(2) $SO_3H$ or cation salt thereof;

(3) $COC_nH_{2n}CO_2H$ wherein n is 1 to 6, or a cation salt thereof;

(4) $CONAC_nH_{2n}CO_2H$ wherein A is as defined in (1), n is 1 to 6, or a cation salt thereof;

(5) $COOC_nH_{2n}CO_2H$ wherein n is 1 to 6, or a cation salt thereof;

(6) $CONA(CHB)CO_2H$ wherein A is as defined in (1) and B is a residue of an amino acid, or a cation salt thereof;

(7) $COCHBNR_1R_2$ wherein B is a residue of an amino acid, $R_1$ and $R_2$ independently are H, $C_1$-$C_6$ alkyl, and phenyl, or an acid addition salt thereof;

(8) $CONAC_nH_{2n}NR_1R_2$ wherein A is as defined in (1), $R_1$ and $R_2$ independently are as defined in (7), n is 2 to 6, and acid addition salts thereof;

(9) $COOC_nH_{2n}R_1R_2$ wherein $R_1$ and $R_2$ independently are as defined in (7), n is 2 to 6, and acid addition salts thereof;

(10) $COC_nH_{2n}NR_1R_2$ wherein $R_1$ and $R_2$ independently are as defined in (7), n is 1 to 6 and acid addition salts thereof; and

(11) COX where X is a leaving group;

The preferred group for R is

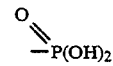

or a cation salt thereof.

By "cation salt" in (1)-(6) above is meant a salt of Li, K, Mg, Na, Ca, ($C_1$-$C_4$alkyl)ammonium.

By "acid addition salt" is meant pharmaceutically acceptable salts such as hydrochloride, hydrobromide, maleate, citrate, tartrate, acetate, succinate and the like.

The amino acids contributing to "B" above include serine, homoserine, ornithine, arginine, histidine, homocystiene, alanine, leucine, isoleucine lysine, methionine, phenylalanine, threonine, valine, glutamine, glycine, phenylalanine, tryptophan and the like.

By a "leaving group" is meant a group which departs with an electron pair. Representative leaving groups are chloride, bromide, iodide and anhydrides of protonated carboxylic acids, sulfonic acids, imidazoles and strongly acidic phenols.

By "neutral pH" is meant pH 6-8.

In referring to compounds hereinafter, the designation "A" following the word "Compound" will refer to a compound of formula (A) and the designations "1", "2", "3" and "4" will indicate the nucleus. Thus, "Compound A-1" will refer to a compound in which U, V and W are all hydroxy; "Compound A-2" to a compound in which U and W are H and V is OH; and "Compound A-3" to a compound in which U is H and V and W are OH. R' and R will be designated by radical names following the number designation.

Preferred compounds are those in which (1) U and W are both OH and (2) U and W are both H, and in which R' is 4-(n-octyloxy)phenyl (OOP), and R is phosphate (Phos) and which may be represented by the following formulas A-1a and A-2a, respectively.

The compounds may be identified also as (1) Compound A-1(OOP-Phos) and (2) Compound A-2(OOP-Phos).

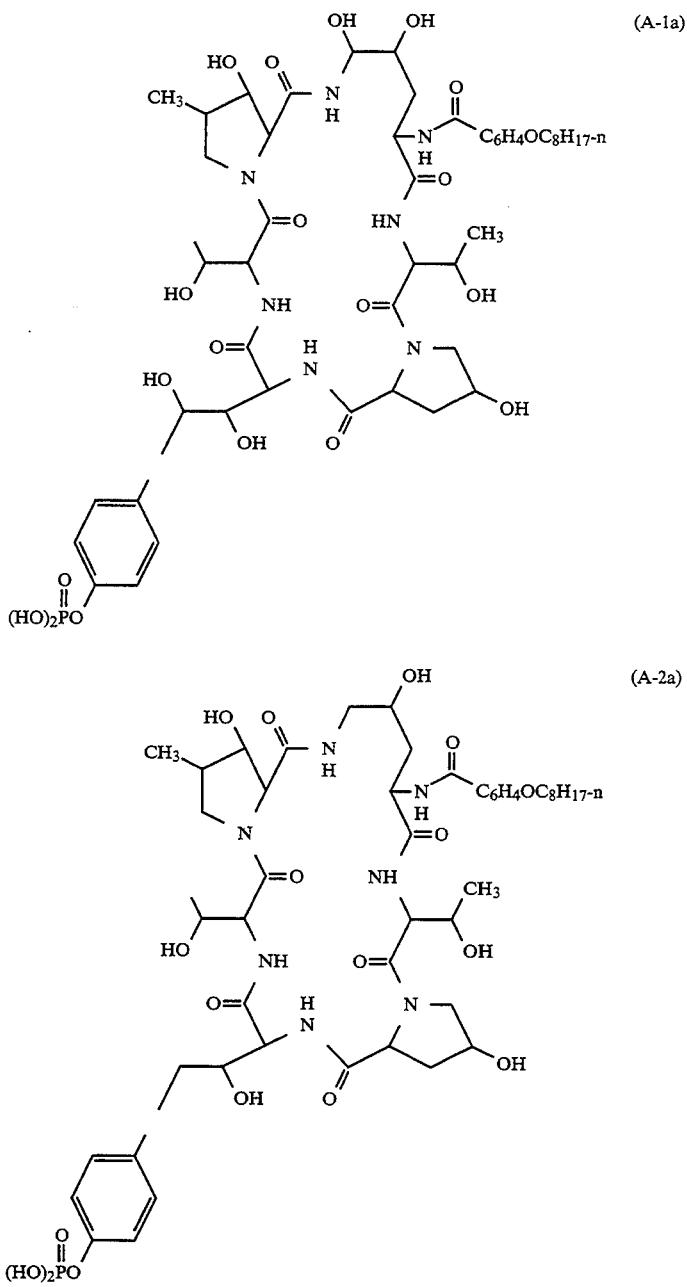

The compounds of the present invention have antifungal and antiprotozoal activity. As antifungal agents, they are useful for the control of both filamentous fungi and yeasts. Among the filamentous fungi which may be controlled are Aspergillus species such as *Aspergillus flavus, Aspergillus fumigatus*, Neurospora species Fusarium species, Alternaria species, and *Cochliobolus miyabeanus* and the like. They are also useful for the treatment of mycotic infections, especially those caused by the Candida organisms such as *C. albicans, C. parapsilosis* and the like. As antiprotozoal agents they may be useful for the control of organisms causing amebiasis such as *Entamoeba histolytica*, or malaria such as Plasmodium species, or other organisms such as Trypanosoma species, Toxaplasma species, Cryptosporidia and the like. They are especially useful for the prevention and or treatment of *Pneumocystis carinii* infections to which immune compromised patients are especially susceptible.

The compounds of the present invention which are generally white or light colored solids are derivatives of antibiotic lipopeptides. Unlike the parent compounds, the present compounds have good solubility properties in water and aqueous media. This property renders the compounds of the present invention more useful as therapeutic agents than the parent compound in many applications. Thus, they are adaptable to being used more readily in injectible compositions. Moreover, the compounds may have a prolonged duration of action.

The compounds of the present invention may be prepared from a lipopeptide having the formula (Z) by acylating at the phenolic hydroxyl and forming an ester link. The lipopeptide having formula Z are natural occurring or semi-synthetic lipopeptides obtained as subsequently described. The overall result may be represented by the following equation:

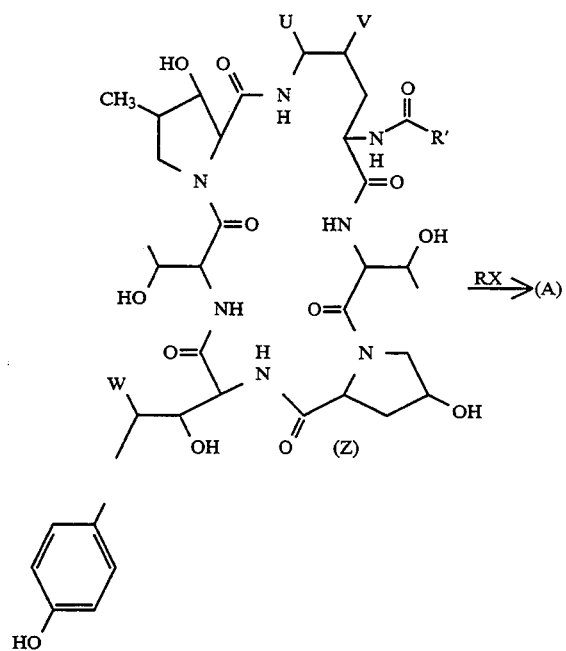

The individual nuclei for the lipopeptide starting material may be seen in the following formulas:

(1) U, V and W are OH

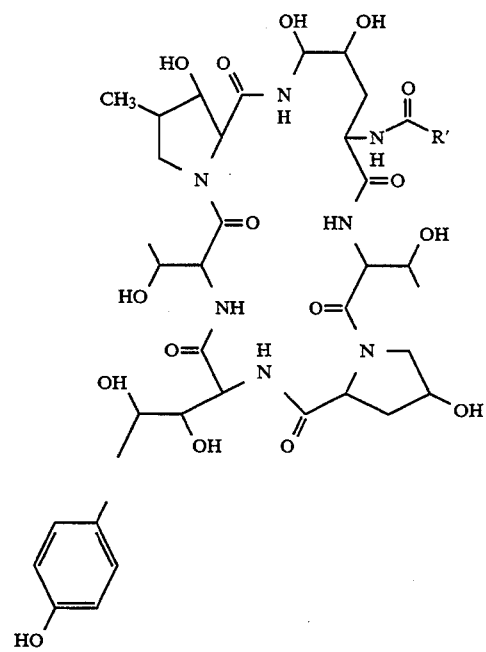

(2) U and W are H and V is OH

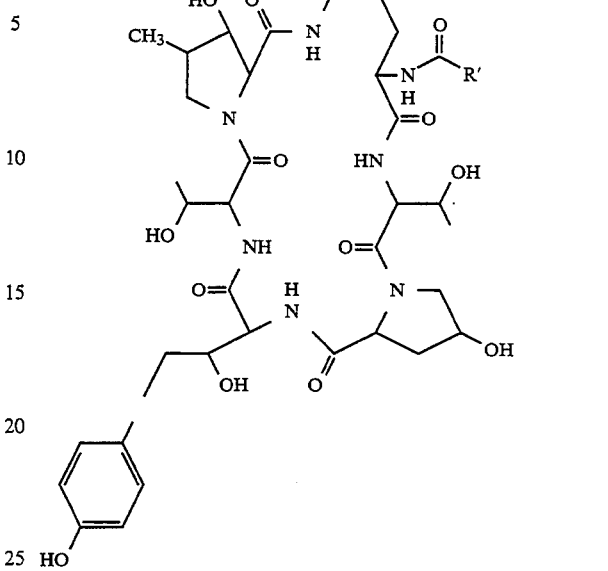

(3) U is H and V and W are OH

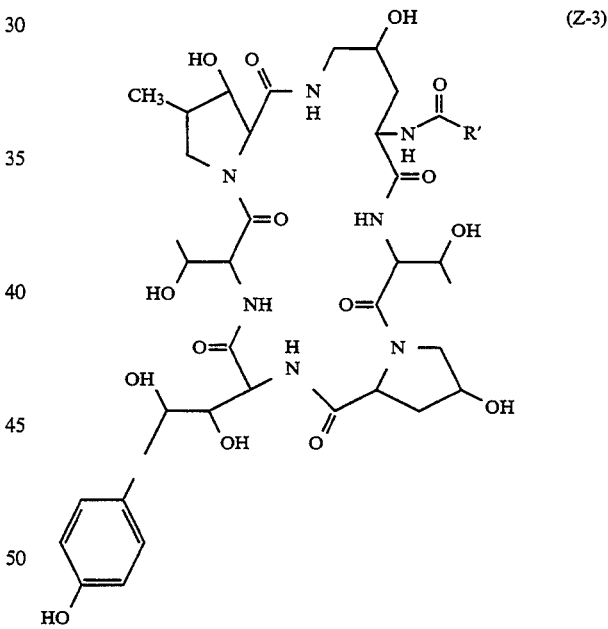

Since the acyl group must have an ionizable group after completion of the acylation, the ionizable group is preferably protected during the acylation and the protecting group removed after completion of the acylation. Moreover, if U is hydroxyl, e.g., formula Z-1, it also may be protected during the acylation. Thus, the preparation of the desired products of the present invention may entail at least one protection/deprotection.

When U in formula (Z) is hydrogen, as in formula Z-2, or Z-3, the compound may be acylated directly. When U in Formula Z is hydroxyl, as in nucleus Z-1 the first step is the etherification of the compound to form an ether, according to the following equation:

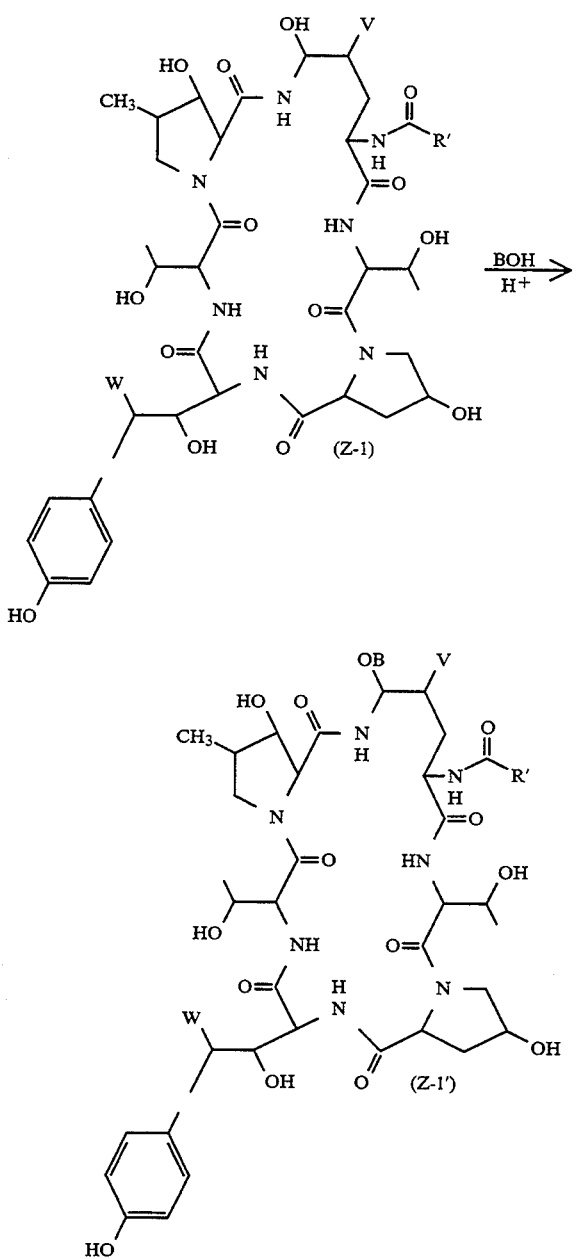

BOH is conveniently benzyl alcohol although other ether forming and readily cleavable alcohols may be employed, such as p-methoxybenzyl alcohol and 2,2,2-trichloroethanol.

The ether formation may be carried out by adding benzyl alcohol and p-toluenesulfonic acid to a solution or dispersion of the lipopeptide in a solvent and stirring at room temperature for from about 16 to 26 hours. The volatiles are then removed in vacuo and the ether product intermediate obtained as residue. The latter may be purified by preparative high performance liquid chromatography (HPLC). The resulting benzyl ether may be employed in the acylation.

The benzyl ether of a Z-1 lipopeptide or a Z-2, or Z-3 lipopeptide is then acylated. The acylation may be carried out by first adding dropwise with stirring at room temperature under an atmosphere of nitrogen, a 1M hexane solution of lithium hexamethyldisilazide (Aldrich) to a pyridine solution of the appropriate lipopeptide or benzyl ether of a lipopeptide and the resulting mixture stirred for 10 to 15 minutes. Then, a solution of RX is added quickly and the resulting mixture stirred from 15 to 60 minutes to obtain the R ester of the lipopeptide or of the benzyl ether of the lipopeptide. The volatiles are then removed in vacuo to obtain the crude ester as a residue. The latter is then purified by preparative high performance liquid chromatography (HPLC) using $H_2O/CH_3CN$ as eluting agent. The eluant fractions having the desired retention time are lyophilized to obtain the desired intermediate ester.

The RX may by any of the compounds which would embraced in the formula using the aforecited definitions for R and for X.

The preferred derivatives of the lipopeptides are phosphate esters. When the ester is a phosphate ester, the preferred esterification intermediate is a dibenzyl phosphate ester. The dibenzyl phosphate ester may be prepared by adding a solution of tetrabenzylpyrophosphate in pyridine to a stirred mixture of lipopeptide or benzyl ether of lipopeptide and lithium hexamethyldisilazide to obtain the dibenzylphosphate ester of the lipopeptide.

The acid or acid salt of the ester may be obtained by low pressure hydrogenolysis of the dibenzylphosphate ester of the lipopeptide or benzyl ether of the lipopeptide. During hydrogenolysis both the benzyl of the phosphate ester and the benzyl of the benzyl ether are cleaved to obtain a phosphate ester of the lipopeptide.

If it is desired to obtain the ultimate ester as its water-soluble salt, the hydrogenolysis may be carried out under mildly alkaline conditions and the desired product recovered as its salt. The free acid may be obtained by controlled acidification.

In one preferred method of carrying out the hydrogenolysis, a solution of dibenzylphosphate in aqueous ethanol is hydrogenated at 1 atmosphere over Pd-C catalyst for 10 to 20 hours whereupon the benzyl of groups the phosphate ester are removed to obtain Compound I as an acid. If the starting lipopeptide is benzyl ether, the benzyl of the ether is also removed. When it is desired to obtain the ultimate ester product as a salt of the acid, the hydrogenolysis medium may be made mildly alkaline with alkali metal bicarbonate and the salt recovered directly. Alternatively, the free acid may be recovered on hydrogenolysis and subsequently converted to the salt by methods known in the art.

When R is a sulfonic acid ester or carboxylic acid ester, the reaction may be carried out in a manner similar to that described for phosphoric acid ester. R may also be a radical in which the charged group at a neutral pH is an ammonium group formed preferably from the amino group of an amino acid which has been esterified at the phenolic hydroxyl.

In certain instances the preferred R may be a sulfate ester as described in specification (2). In these cases the sulfate ester may be prepared directly by treatment of a solution of the lipopeptide or lipopeptide benzyl ether in pyridine with sulfur trioxide pyridine complex to produce the pyridinium sulfate ester. If the free acid is desired it may be obtained by acidification with a strong acid such as hydrochloric acid followed by purification using a "Zorbax" C8 reverse phase HPLC column as stationary phase. If the lipopeptide benzyl ether is employed the benzyl ether may be removed by hydrogenolysis as described above.

When RX is a carboxylic acid derivative the preferred reagents for acylation are the carboxylic acid chlorides and anhydrides. The incipient charged group if it is to be a carboxylic acid salt may preferably be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus, in one preferred esterification, the lipopeptide or lipopeptide benzyl ether in pyridine containing 4-dimethylaminopyridine as catalyst is treated with the symmetrical anhydride of the carboxylic acid to produce the carboxylic ester. Deprotection preferably by hydrogenolysis of the benzyl ester, if the charged group is to be an acid, or by hydrogenolysis of the benzyloxycarbonyl group, if the charged group is to be an amine, then releases carboxylic acid or amine respectively. If the charged group is to be an acid then the hydrogenolysis may be carried out under mildly alkaline conditions to obtain the water soluble salt directly. Conversely if the charged group is to be amine base the hydrogenolysis may be carried out under mildly acidic conditions to obtain the water soluble ammonium salt directly.

It certain instances such as in (4), (6), and (8) above the ester linkage forms a portion of a carbamate. In those cases where A as defined in (1) above is hydrogen, the preferred reagent for acylation is the isocyanate. The incipient charged group if it is to be a carboxylic acid salt preferably may be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus in a preferred esterification, the lipopeptide or lipopeptide benzyl ether in pyridine containing 4-dimethylaminopyridine is treated with the isocyanate to produce the carbamate. Deprotection may then proceed in a preferred case by hydrogenolysis as described above to release the charged group. In those instances in which A is other than hydrogen as defined in (1) above, a different procedure must be used. In these cases a preferred method involves initial formation of a reactive carbonate. Thus a solution of the lipopeptide or lipopeptide benzyl ether in pyridine containing 4-dimethylaminopyridine is treated with p-nitrophenylchloroformate and in this way the mixed p-nitrophenylcarbonate is prepared. In a separate step the p-nitrophenylcarbonate is converted to the desired carbamate. Treatment of the p-nitrophenylcarbonate in dimethylformamide with a secondary amine provides the protected carbamate. Deprotection may then proceed in a preferred case by hydrogenolysis as described above to unveil the charged group and provide the compounds described in (4), (6) and (8) above where A is other than hydrogen.

When compounds such as those described in specifications (5) and (9) above are desired the ester link forms a portion of a carbonate. In these cases the preferred reagents for acylation are the chloroformates. The incipient charged group if it is to be a carboxylic acid salt preferably may be protected during the acylation reaction as a benzyl ester or other easily removed esters such as 2,2,2-trichloroethyl esters or allyl esters. If the incipient charged group is to be an ammonium species, the amine is conveniently protected during the acylation procedure as its benzyloxycarbonyl derivative. Other protecting groups for the ammonium group may include t-butoxycarbonyl or 2,2,2-trichloroethoxycarbonyl or other protecting groups well known to those skilled in the art. Thus, in a preferred esterification, the lipopeptide or lipopeptide benzyl ether in pyridine containing 4-dimethylaminopyridine is treated with the chloroformate to produce the carbonate. Deprotection may then proceed in a preferred case by hydrogenolysis as described above to release the charged group.

The compound of the present invention are useful as antifungal agents, both against filamentous fungi and yeasts, and they are also useful as antiparasital agents, especially against protozoal parasites. As antifungal agents, the compounds are useful against Candida species as but they may also be employed against filamentous fungi such as *Aspergillus flavus, Aspergillus fumigatus, Aspergillus niger, Cochliobolus miyabeanus* and the like. In addition the compounds may be employed as antiparasital or antiprotozoal agents. They may be useful for the control of organisms causing amebiasis such as *Entamoeba histolytica,* or organisms causing malaria such as Plasmodium species, or other organisms such as Trypanosoma species and the like. They are especially useful in inhibiting or alleviating *Pneumocystis carinii* infections. In such use, Compound I or a composition containing Compound I is administered in a therapeutically effective or inhibitory amount to subjects infected with or susceptible to being infected with *Pneumocystis carinii.*

The outstanding properties are most effectively utilized when the compound is formulated into novel pharmeceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound A or one of the components. Concentrate compositions suitable for dilutions prior to use may contain 90% or more by weight. The compositions include compositions suitable for rectal, topical, parenteral (including subcutaneous, intramuscular, and intravenous), pulmonary (nasal or buccal inhalation), nasal administration, or insufflation. The compositions may be prepacked by intimately mixing Compound A with the components suitable for the medium desired.

When the compound is for antifungal use any method of administration may be used. For treating mycotic infection oral administration is frequently preferred. When oral administration is to be employed, it may be with a liquid composition or a solid composition. For liquid preparations, the therapeutic agent is formulated with liquid carriers such as water, glycols, oils, alcohols, and the like, and for solid preparations such as capsules and tablets, it is formulated with solid carriers such as starches, sugars, kaolin, ethyl cellulose, calcium and sodium carbonate, calcium phosphate, kaolin, talc, lactose, generally with lubricant such as calcium stearate, together with binders, disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Composition in unit dosage form constitutes an aspect of the present invention.

The Compound A also may be formulated in therapeutic compositions for intravenous or intraperitoneal injection and may be presented in unit dosage form in ampoules or in multidose containers, if necessary, with an added preservative. The compositions may also take such forms as suspensions, solutions or emulsions in oily or aqueous vehicles such as 0.85 percent sodium chloride or 5 percent dextrose in water, and may contain formulating agents such as suspending stabilizing and/or dispersing agents. Buffering agents as well as additives such as saline or glucose may be added to make the solutions isotonic. The drug also may be solubilized in alcohol/propylene glycol or polyethyleneglycol for drip intravenous administration. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 100 to 200 milligrams of one of the compounds.

When the compound is to be employed for control of pneumocystis infections it is desirable to directly treat lung and bronchi. For this reason, inhalation methods are preferred. For administration by inhalation, the compounds of the present invention are conveniently delivered in the form of an aerosol spray presentation from pressurized packs of nebulisers. The preferred delivery system for inhalation is a metered dose inhalation (MDI) aerosol, which may be formulated as a suspension or solution of Compound A in suitable propellants, such as fluorocarbons or hydrocarbons.

Although the compounds of the present invention may be employed as tablets, capsules, topical compositions, insufflation powders, suppositories and the like, the advantage of the derivatives of the present invention over the parent lipopeptide is in their water solubility. Hence, the compounds of the present invention are most effectively utilized in injectible formulations and also in liquid compositions suitable for aerosol sprays.

Compound A also may be employed against a broad spectrum of yeasts and filamentous fungi (molds). For non-medical application, the product of the present invention, may be employed in compositions in an inert-carrier which includes finely divided dry or liquid diluents, extenders, fillers, conditioners and excipients, including various clays, diatomaceous earth, talc, and the like, various organic liquids such as lower alkanols, for example, ethanol and isopropanol, or kerosene, benzene, toluene and other petroleum distillate fractions or mixtures thereof. However, as with medical applications, the compounds are best utilized in aqueous compositions.

The following examples illustrate the invention but are not to be construed as limiting:

EXAMPLE I

1-[4,5-dihydroxy-N2-(4-octyloxybenzoyl)ornithine-4-[3,4-dihydroxy-4'-O-phosphoryl-homotyrosine]-echinocandin B disodium salt (I)

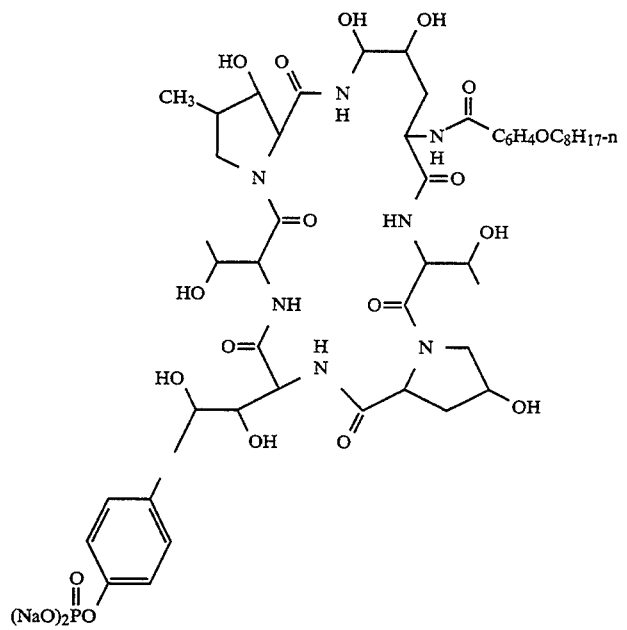

(I) (Compound A-1a)

Part A. Benzyl Ether

1-[4-hydroxy-5-benzyloxy-N2-(4-octyloxybenzoyl-ornithine]echinocandin B (Ia)

Part B. Dibenzylphosphate Ester

1-[4-hydroxy-5-benzyloxy-N2-(4-octyloxybenzoyl-ornithine]-4-[3,4-dihydroxy-4'-O,O-dibenzylphosphoryl-homotyrosine]-echinocandin B (Ib)

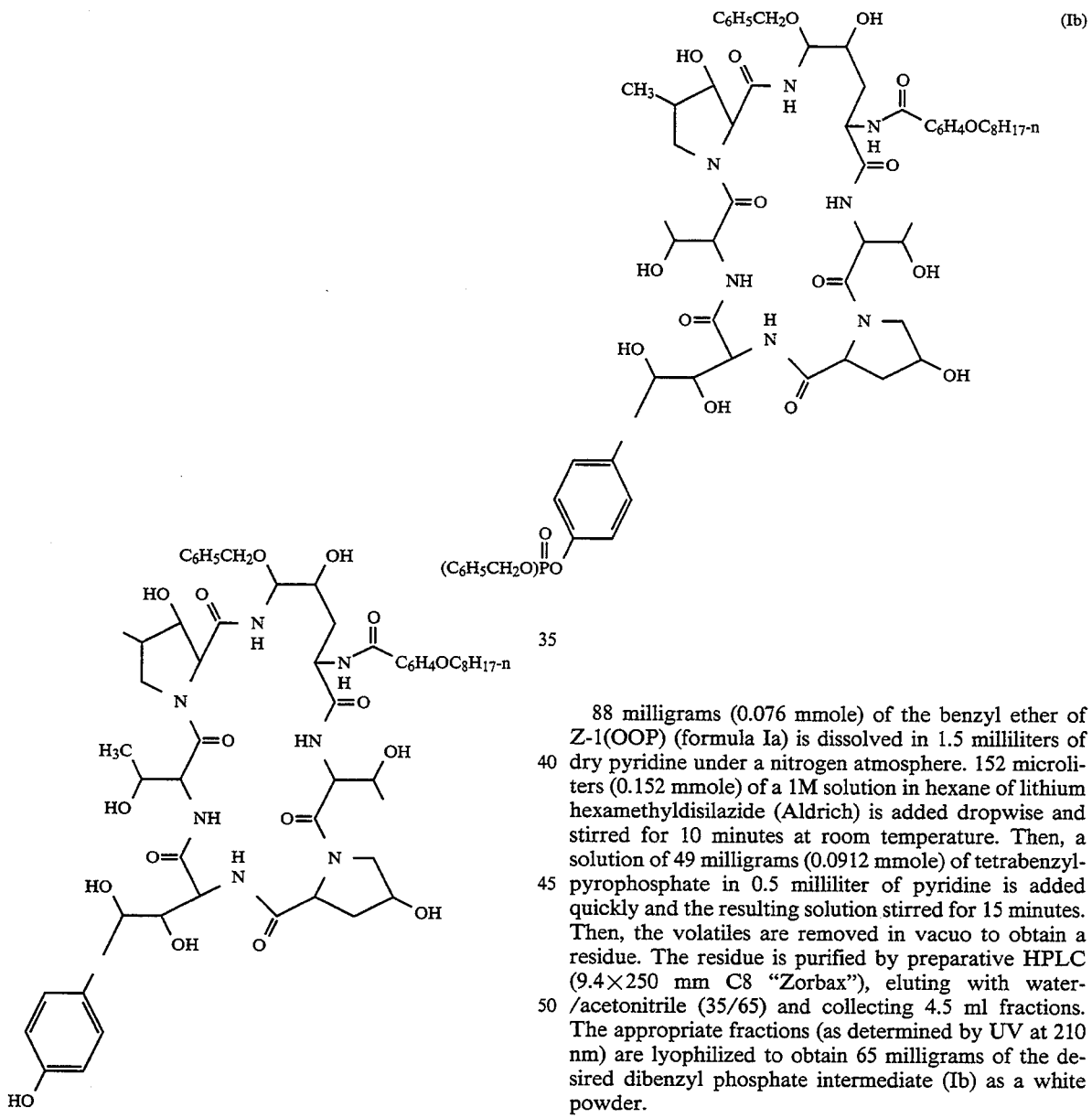

350 mg of 1-[4,5-dihydroxy-N2-(4-octyloxybenzoyl]-ornithine]-echinocandin B (Compound Z-1(OOP)) is suspended in 7 milliliters of tetrahydrofuran and to the suspension is added 0.68 milliliter of benzyl alcohol and 7 milligrams of p-toluenesulfonic acid. The mixture remains heterogeneous; 3 milliliters of dimethylformamide is added and the resulting solution stirred for 24 hours at room temperature. At the end of this period, the volatiles are removed in vacuo to obtain a residue which is purified by preparative HPLC (21.2×250 mm C8 "Zorbax" (DuPont)) eluting with water/acetonitrile (40/60) at 10 ml/min. and collecting 15 milliliter fractions. The appropriate fractions (as determined by UV at 210 nm) are combined and lyophilized to obtain the benzyl ether intermediate (Ia) as a white solid.

88 milligrams (0.076 mmole) of the benzyl ether of Z-1(OOP) (formula Ia) is dissolved in 1.5 milliliters of dry pyridine under a nitrogen atmosphere. 152 microliters (0.152 mmole) of a 1M solution in hexane of lithium hexamethyldisilazide (Aldrich) is added dropwise and stirred for 10 minutes at room temperature. Then, a solution of 49 milligrams (0.0912 mmole) of tetrabenzyl-pyrophosphate in 0.5 milliliter of pyridine is added quickly and the resulting solution stirred for 15 minutes. Then, the volatiles are removed in vacuo to obtain a residue. The residue is purified by preparative HPLC (9.4×250 mm C8 "Zorbax"), eluting with water-/acetonitrile (35/65) and collecting 4.5 ml fractions. The appropriate fractions (as determined by UV at 210 nm) are lyophilized to obtain 65 milligrams of the desired dibenzyl phosphate intermediate (Ib) as a white powder.

Part C. Preparation of Sodium Salt Phosphate Ester (Hydrogenolysis of Dibenzylphosphate)

62 milligrams (0.0438 mmole) of the intermediate (Ib) above obtained is dissolved in 6 milliliters of water/ethanol (1:1>and to it is added a solution of 7.4 mg (0.0875 mmole) of sodium bicarbonate in distilled water. Next 60 milligrams of 10% Pd-C is added and the mixture stirred under 1 atmosphere of hydrogen at room temperature for 7 hours. The mixture is then filtered through a 0.2 micron filter, washed with 1:1 ethanol/-water and concentrated on a rotary evaporator. The residue is lyophilized to obtain the product as a white solid. The molecular weight of Compound I is 1109 as the free acid.

EXAMPLE II

1-[4-hydroxy-N2-(4-octyloxybenzoyl-ornithine]-4-[3-hydroxy-4'-O-phosphoryl-homotyrosine]-echinocandin B disodium salt (II)

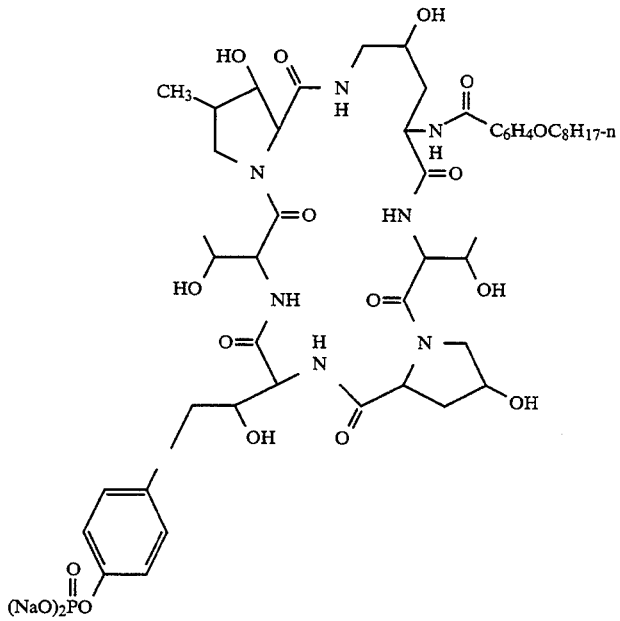

(II) (Compound A-2a)

Part A. Dibenzylphosphate Ester

1-[4-hydroxy-N2-(4-octyloxybenzoyl)ornithine]-4-[3-hydroxy-4'-O,O-dibenzylphosphoryl-homotyrosine]echinocandin B

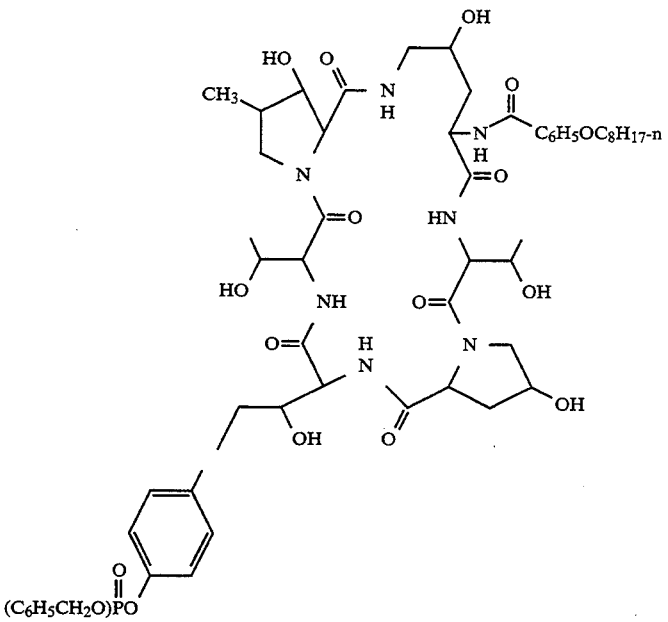

(IIb)

To a solution of 1 gram (1.0 mmol) of 1-[4-hydroxy-N2-(4-octyloxybenzoyl)ornithine-4-[3-hydroxy-homotyrosine]-echinocandin B in 25 ml of dry pyridine is added dropwise with stirring under an atmosphere of nitrogen at room temperature, 1.43 milliliter of a 1M solution in hexane of lithium hexamethyldisilazide. The resulting solution is stirred at room temperature for 10 minutes and to it is rapidly added a solution of 566 milligrams (1.05 mmole) of tetrabenzylpyrophosphate in 5.0 milliliters of pyridine. The resulting yellow solution is stirred for one hour after which an additional 100 milligrams of pyrophosphate is added as a solid. After 10 minutes, another 100 milligrams of the phosphorylating agent is added and the mixture stirred. The volatiles are removed in vacuo to obtain a residue. A HPLC analysis of the latter on C8 "Zorbax" employing water/acetonitrile (30/70) at 2 ml/min. shows the reaction to be nearly complete. The material is divided into three portions and each is purified by preparative HPLC on 21.2×250 mm C8 Zorbax eluting with water/acetonitrile (40/60) at 12 ml/min. The fractions are collected and lyophilized to obtain the desired dibenzyl phosphate intermediate as a white powder.

Part B. Phosphoric Acid Ester of Z-2

1-[4-hydroxy-N2-(4-octyloxybenzoyl-ornithine)-4-[3-hydroxy-4'-O-phosphoryl-homotyrosine]-echinocandin B disodium salt The dibenzyl phosphate prepared as described in Part A (470 milligrams, 0.36 mmol) is dissolved in 20 milliliters of absolute ethanol. To it is added a solution of 60.5 milligrams (0.72 mmol) of sodium bicarbonate in 10 milliliters of water followed by 157 milligrams of 10% Pd-C and the mixture stirred under 1 atmosphere of hydrogen at room temperature for four hours. At the end of this period, the mixture is filtered, washed with 1:1 ethanol/water and concentrated. The product is purified in four units by preparative HPLC (21.2×250 mm C8 Zorbax, water/acetonitrile (55/45) at 12 ml/min, 4.8 milliliter fractions) and the appropriate fractions concentrated and lyophilized to obtain the desired product as a white powder. The molecular weight of Compound II is 1077 as the free acid.

EXAMPLE III

1-[4,5-dihydroxy-N2-(4-octyloxybenzoyl)ornithine]-4-[3,4-dihydroxy-4'-O-(2-N-methylcarbamoylacetic acid)-homotyrosine]-echinocandin B (III)

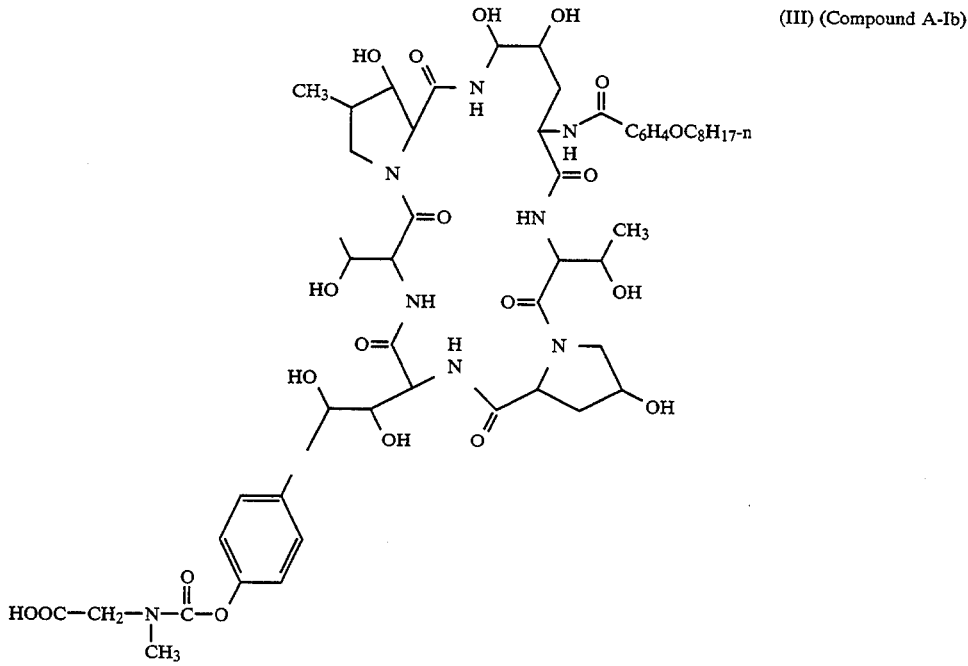

(III) (Compound A-Ib)

Part A. Benzyl Ether

In a manner similar to that described in Example I, 0.68 ml of benzyl alcohol and 7 mg of p-toluenesulfonic acid are added to a solution of 350 mg of Compound Z-1(OOP) in a mixture of 7 ml of tetrahydrofuran and 3 ml of dimethylformamide and the mixture stirred at room temperature for 24 hours. At the end the volatiles are removed in vacuo to obtain a residue which is purified on a preparative HPLC column using water/acetonitrile (40/60) as eluant. The appropriate fractions are combined and lyophilized to obtain benzyl ether of Z-1(OOP).

Part B. p-Nitrophenyl Carbonate

1-[4-hydroxy-5-benzyloxy-N2-(4-octyloxybenzoyl)ornithine]-4-[3,4-dihydroxy-4'-O-p-nitrophenyl-carbonate-homotyrosine]-echinocandin B

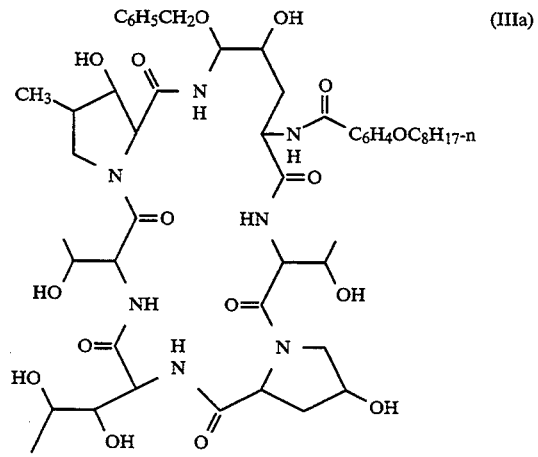

(IIIa)

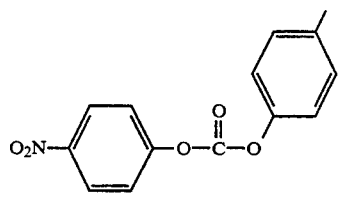

To a solution of the 0.262 g (0.234 mmol) benzyl ether of Z-1 (OOP) prepared in Part A in 2.5 ml of dry pyridine is added sequentially 31 mg (1.1 eq) 4-dimethylaminopyridine and 52 mg (1.1 eq) of p-nitrophenyl chloroformate and the mixture allowed to stir at room temperature for 20 hours. At the end of this period, the mixture is concentrated in vacuo and the residue dissolved in water/acetonitrile and thereafter purified by preparative reverse phase chromatography, eluting with water/acetonitrile. The fractions containing the desired product are concentrated in vacuo to remove the acetonitrile and then lyophilized to obtain purified p-nitrophenyl carbonate ester.

Part C. 1-[4,5-dihydroxy-N2-(4-octyloxybenzoyl)ornithine]-4-[3,4-dihydroxy-4'-O-(2-N-methylcarbamoylacetic acid)-homotyrosine]echinocandin B To a solution of 100 mg (0.081 mmol) of the p-nitrophenyl carbonate prepared as described in Part B in 1 ml of dry dimethylformamide is added 15 mg (1.1 eq) of benzyl sarcosine and the mixture allowed to stir at room temperature for 20 hours. The crude reaction mixture is concentrated in vacuo, the residue dissolved in water/acetonitrile and purified by reverse phase chromatography on "Zorbax" C8 column and eluted with acetonitrile/water. The fractions containing the desired intermediate is concentrated in vacuo to remove the acetonitrile and then lyophilized to obtain a purified benzyl ester.

The ester is dissolved in 15 ml of absolute ethanol and to the solution is added 15 mg of 10% Pd-C and stirred at 1 atmosphere of hydrogen for 5 hours. At the end of this period, the mixture is filtered and the filtrate concentrated to obtain the desired product (III). The product is purified on preparative HPLC employing water/acetonitrile. The molecular weight of III is 1144.

EXAMPLE IV

In similar operations, the following compounds are prepared when R' is —$C_6H_4OC_8H_{17}$—n and V is OH:

| Compound No. | U | W | R |
|---|---|---|---|
| IV | OH | OH | $SO_3H$ |
| V | H | OH | $\overset{O}{\underset{\|}{P}}(ONa)_2$ |
| VI | H | OH | $\overset{O}{\underset{\|}{P}}(ONa)_2$ |
| VII | H | OH | $SO_2ONa$ |
| VIII | H | OH | $COCH_2COOH$ |
| IX | H | OH | $CONH(CH_2)_2COOH$ |
| X | H | OH | $CO(CH_2)_2NH_2.HCl$ |
| XI | H | H | $CONH(CH_2)_2NH_2.HCl$ |
| XII | H | H | $\overset{O}{\underset{\|}{P}}(OH)_2$ |
| XIII | H | H | $COOCH_2COOH$ |
| XIV | OH | OH | $CON(CH_3)(CH_2)_2COOH$ |
| XV | OH | OH | $COCH(CH_2C_6H_5)NH_2.HCl$ |
| XVI | OH | OH | $COCH_2NH_2.HCl$ |
| XVIII | OH | OH | $COOCH_2NH_2.HCl$ |

EXAMPLE V

In similar operations, the following compounds are prepared when R' is n-heptadecyl and V is OH:

| Compound No. | U | W | R |
|---|---|---|---|
| XVIII | OH | OH | $SO_3H$ |
| XIX | H | OH | $\overset{O}{\underset{\|}{P}}(ONa)_2$ |
| XX | H | OH | $\overset{O}{\underset{\|}{P}}(ONa)_2$ |
| XXI | H | OH | $SO_2ONa$ |
| XXII | H | OH | $COCH_2COOH$ |
| XXIII | H | OH | $CONH(CH_2)_2COOH$ |
| XXIV | H | OH | $CO(CH_2)_2NH_2.HCl$ |
| XXV | H | H | $CONH(CH_2)_2NH_2.HCl$ |
| XXVI | H | H | $\overset{O}{\underset{\|}{P}}(OH)_2$ |
| XXVII | H | H | $COOCH_2COOH$ |
| XXVIII | OH | OH | $CON(CH_3)(CH_2)_2COOH$ |
| XXIX | OH | OH | $COCH(CH_2C_6H_5)NH_2.HCl$ |
| XXX | OH | OH | $COCH_2NH_2.HCl$ |
| XXXI | OH | OH | $COOCH_2NH_2.HCl$ |

In the following examples "Compound" followed by a Roman numeral designation refer to the compound in the example corresponding to the Roman numeral.

EXAMPLE VI 1000 hard gelatin capsules, each containing 500 mg of Compound IB are prepared from the following formulation:

| Compound | Grams |
|---|---|
| Compound III | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE VII 250 ml of an injectable solution are prepared by conventional procedures having the following formulation:

| Dextrose | 12.5 g |
|---|---|
| Water | 250 mL |
| Compound A-1a (or I) | 400 mg |

The ingredients are blended and thereafter sterilized for use.

EXAMPLE VIII 250 ml of an injectable solution are prepared by conventional procedures having the following formulation:

| Dextrose | 12.5 g |
|---|---|
| Water | 250 ml |
| Compound A-2a (or II) | 400 mg |

The ingredients are blended and thereafter sterilized for use.

EXAMPLE IX

An ointment suitable for topical application may be prepared by intimately dispersing 13 mg of Compound A-2a in 1 g of commercially available polyethylene/hydrocarbon gel.

EXAMPLE X

An injectable solution similar to that of Example VIII except that Compound IV is substituted for Compound II is prepared.

EXAMPLE XI 1000 hard gelatin capsules, each containing 500 mg of Compound II, are prepared from the following formulation:

| Compound | Grams |
|---|---|
| Compound II | 500 |
| Starch | 250 |
| Lactose | 750 |
| Talc | 250 |
| Calcium Stearate | 10 |

The components are uniformly blended and used to fill two-piece hard gelatin capsules.

EXAMPLE XII

An aerosol composition may be prepared having the following formulation:

| | Per Canister |
|---|---|
| Compound I | 24 mg |
| Lecithin NF Liquid Concentrate | 1.2 mg |
| Trichlorofluoromethane, NF | 4.026 g |
| Dichlorodifluoromethane, NF | 12.15 g |

Starting Materials

Some of the lipopeptide starting materials are natural products, produced by fermentation, while some are semi-synthetic peptides which have been obtained by modification of the natural product.

Natural products which are starting materials for the present invention include those which are described in the literature as echinocandins, aculeacins, mulundocandins, athlestain (also referred to as an echinocandin T), sporiofungin or by number designations. The structures in some cases are not completely identified but the compounds are known to be neutral cyclohexapeptides with a fatty acid side chain. Whatever their original name designation, they are now understood to belong to the class echinocandins.

The echinocandins natural products generally have a linoleyl side chain, i.e. R' in formula A is $-(CH_2)_7CH=CHCH_2CH=CH(CH)_4CH_3$. Echinocandin B is the most important of the natural product echinocandins. In echinocandin B, U, V and W in structure A is OH.

Echinocandin B may be produced on the fermentation of *Aspergillus rugulosus* as described in Helv. Chem. Aeta 62, 11252; (1979); Ger 2,549, 127; and Belg. 834,289. Echinocandin C (U & V are OH and W is H) and Echinocandin D (U & V are H and W is H) may also be produced as minor metabolites in the same fermentation. Echinocandin B also may be produced by the cultivation of *Emericella nidulans*. Other antibiotic cyclohexapeptides including such as mulundocandin (R' is $-(CH_2)_{10}CH(CH_3)CH_2CH_3$) reported in J. Antibiotics 40, 275 and 40, 281 (1987), are identified as natural occurring starting materials which may be employed.

Compounds which are modifications of natural products include those in which the side chain, i.e., R', when an unsaturated fatty radical acid, which had been modified by reduction. This may be carried out catalytically, by using Pd on carbon at atmospheric pressure.

Semi-synthetic compounds in which the acyl side chain, i.e.,

in above formula, has been modified from naturally occurring fatty acids to structurally distinctive acyl group may be produced by first removing the fatty acid side chain and thereafter introducing a distinctive acyl group. The fatty acid side chain preferably is removed enzymatically by enzymes produced, for example, by certain microorganisms of the family Actinoplanaceae, especially the microorganism *Actinoplanes utahensis* NRRL 12052 which is available from the Northern Regional Research Center, USDA, Agri. cultural Research Service, Peoria, Ill. 61604, or as *A. utahensis* ATCC 14539 obtainable from the American Type Culture Collection, 12301 Parklawn Drive, Rockville, Md. 20852.

The enzyme may be produced by growing Actinoplanaceae at temperatures between about 25° C. and 30° C. and a pH of between about 5.0 and 8.0, preferably between 6.0 and 7.0, with agitation and aeration for from about 40 to about 60 hours in a culture medium containing (a) an assimilable carbon source such as sucrose, glucose or glycerol, (b) a nitrogen source such as peptone, urea or ammonium sulfate (c) a phosphate source such as a soluble phosphate salt and (d) growth promoting inorganic salts.

In the deacylation, the cyclohexapeptide compound or substrate containing the cyclohexapeptide is added to the culture of Actinoplanaceae after the culture has been incubated for at least 48 hours. After addition of the substrate, the incubation of the culture is continued for about 24 hours or longer over temperatures in the range of from about 25° C. to about 30° C.

The course of the reaction may be monitored by *Candida albicans* assay. The starting cyclohexapeptide compound is active against *C. albicans* but the deacylated nucleus compound is biologically inactive.

The deacylated nucleus compound then may be employed in the preparation of semi-synthetic compounds. Conventional acylation methods may be employed. In one preferred method, a 2,4,5-trichlorophenyl ester of the desired acid is reacted with the deacylated nucleus compound in an inert solvent such as dimethylformamide at room temperature for about 15 to 18 hours.

The preparation of the deacylated cyclohexapeptide compound having the same nucleus from echinocandin type natural products is more fully described in U.S. Pat. No. 4,293,482. Similar preparations of other deacylated cyclohexapeptide compounds with similar nuclei may be found described in U.S. Pat. Nos. 4,173,629; 2,493,490; 4,299,763; 4,299,762; and 4,304,716.

The deacylated compounds may then be employed to produce novel and/or unusual acylated compounds.

The acylation of the compound of the deacylated nucleus, to produce a unique acyl derivative may be illustrated with a preparation of a compound in which R′ is

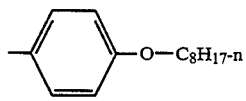

In the acylation, the acyl group is preferably introduced by means of a trichlorophenyl ester. Thus, first, the trichlorophenyl ester may be prepared by treating the side chain acid with 2,4,5-trichlorophenol in the presence of a coupling agent such as N,N′-dicyclohexylcarbodiimide in an inert solvent such as methylene chloride. About 1.1 mole of the 2,4,5-trichlorophenol and 1.0 mole of the coupling agent is used for each mole of the alkoxybenzoic acid. The mixture is stirred at room temperature for 15 to 18 hours to obtain the ester which may be recovered by filtering the solid and evaporating the filtrate under reduced pressure, then recrystallizing the residue.

The ester thus prepared is added to a solution of the nucleus compound in dimethylformamide and stirred for about 18 hours and then the solvent evaporated off. The residue is washed and then chromatographed on silica gel using ethyl acetate-methanol (3/2) as eluant to obtain the desired octyloxybenzoyl derivative which may be represented in formula A with the octyloxyphenyl group as R′. Such a compound may be named 1-[-4,5-dihydroxy-N²-[4-(octyloxy)benzoyl]-L-ornithine]echinocandin B.

The derivatives of the present invention in which U, or U and W are hydrogen may be prepared by the reduction of the natural or semisynthetic echinocandin type lipopeptides in which U and W are hydroxyl. The reduction may be carried out by intimately mixing the lipopeptide and reducing agent in a strong acid medium. Suitable reducing agents are sodium cyanoborohydride, triethyl silicon hydride and sodium borohydride. Suitable strong acids include trifluoroacetic acid and trichloroacetic acid. When it is desired to obtain a mono-reduced product, namely one in which the hydroxyl OH at U is reduced but W remains hydroxyl, it is preferred to include an acid other than the foregoing strong acid. Glacial acetic acid is a suitable acid.

The preparation may be illustrated with the preparation of semisynthetic intermediates which may be starting materials.

EXAMPLE A

This example illustrates the preparation of a compound in which U and W are H, V is OH and R′ is —C₆H₄OC₈H₁₇—n.

21 mg (0.021 mmol) of 1-[4,5-dihydroxy-N2-[4-(octyloxy)benzoyl]ornithine]echinocandin B (Compound Z- a, R′=—C₆H₂OC₈H₁₇—n) was suspended in 2.0 milliliters of dichloromethane and to it was added 0.10 milliliters (1.3 millimoles) trifluoroacetic acid. 14 milligrams (0.22 millimole) of sodium cyanoborohydride was added to the homogeneous reaction mixture in one portion. The resulting mixture was stirred at room temperature for 2 hours and a small amount of methanol was added and the volatiles were removed in vacuo. The resultant solid was purified by reverse phase HPLC (2.12×25 cm C8 "Zorbax") and eluted with water-/acetonitrile (50/50) at 10 milliliter per minute in 6 milliliter fractions. Fractions 22–27 contained the bulk of the product and the combined fractions were lyophilized to yield 10.9 milligrams (54 percent) of a fluffy white solid.

$^1$H-NMR: (300 MHz, CD₃OD): δ 7.02 (d, J=9Hz), 3.72. (dd, J=14, 4.8 HZ).

Mass Spectrum (FAB): 998 (M+1).

EXAMPLE B

In a similar manner, to 100 mg (0.1 mmol) of tetrahydroechanocandin B (Compound Z-1b, R′=heptadecyl) (obtained by reduction of natural product echinocandin B with hydrogen over Pd/C), in 48 milliliters of dichloromethane and 2.38 milliliters of trifluoroacetic acid was added 333 milligrams of sodium cyanoborohydride to obtain Compound Z-26, (R=heptadecyl) intermediate which was recovered by concentrating in vacuo and purified by reverse phase HPLC as a fluffy white solid. The intermediate had the following physical properties:

$^1$H-NMR (300 MHz, CD₃OD): δ 7.03 (d, J=9 Hz), 3.70 (dd, J=14, 3.9 Hz).

Mass Spectrum (FAB), 1038 (Li⁺ spike).

EXAMPLE C

In a similar manner, bisdeoxyechinocandin B (Compound Z-2, R′=—(CH₂)₇CH=CHCH₂CH=CH(CH₂)₄CH₃) was obtained by the reaction of echinocandin B and sodium cyanoborohydride. The intermediate had the following physical constants:

$^1$H-NMR (300 MHz, CD₃OD): δ 7.01 (d, J=8 Hz, 2H), 5.33 (m, 4H), 3.68 (dd, J=14, 3.4Hz, 2.96 (dd, J=14, 4.0 Hz, 1H).

Mass Spectrum (FAB): 1048 (M+1).

What is claimed is:

1. A compound having the formula:

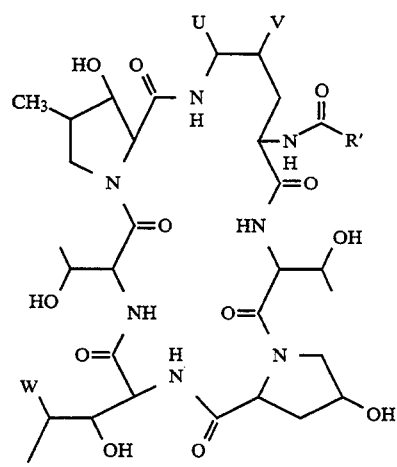

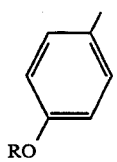

wherein

R is acyl, phosphono or sulfo radical which possesses a charged group at neutral pH;

R' is a $C_5$-$C_{23}$ alkyl, $C_5$-$C_{23}$ alkenyl or $C_5$-$C_{23}$ alkynyl or aryl;

U, V and W are independently H or OH.

2. A compound having the formula

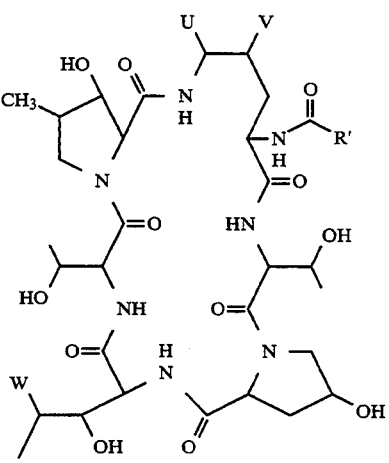

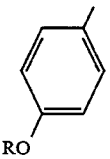

wherein

U, V and W are independently H or OH, selected from those in which (1) U, V and W are all OH; (2) U and W are H and V is OH; and (3) U is H and V and W are OH;

R' is $C_5$-$C_{23}$ alkyl, $C_5$-$C_{23}$ alkenyl, $C_5$-$C_{23}$ alkynyl or aryl;

R is
(1) $PO_3AH$ wherein A is H, $C_1$-$C_6$ alkyl, phenyl or substituted phenyl wherein the substituent may be alkyl, alkyloxy, alkylthio, or alkylamino or a Li, Na, K, Mg and Ca cation salt thereof;
(2) $SO_3H$ or cation salt thereof; as defined in (1);
(3) $COC_nH_{2n}CO_2H$ wherein n is 1 to 6 or a cation salt thereof as defined in (1);
(4) $CONAC_nH_{2n}CO_2H$ wherein A is as defined in (1), n is 1 to 6, or a cation salt thereof as defined in (1);
(5) $COOC_nH_{2n}CO_2H$ wherein n is 1 to 6, or a cation salt thereof as defined in (1);
(6) $CONA(CHB)CO_2H$ wherein B is a residue of an amino acid, or a cation salt thereof as defined in (1);
(7) $COCHBNR_1R_2$ wherein B is a residue of an amino acid, $R_1$ and $R_2$ independently are H, $C_1$-$C_6$ alkyl, and phenyl, and acid addition salts thereof;
(8) $CONAC_nH_{2n}NR_1R_2$ wherein A is as defined in (1), $R_1$ and $R_2$ independently are as defined in (7), n is 2 to 6, and acid addition salts thereof;
(9) $COOC_nH_{2n}R_1R_2$ wherein $R_1$ and $R_2$ independently are as defined in (7), n is 2 to 6, and acid addition salts thereof; and
(10) $COC_nH_{2n}NR_1R_2$ wherein $R_1$ and $R_2$ independently are, as defined in (7), n is 1 to 6 and acid addition salts thereof.

3. An antimicrobial composition comprising a compound of claim 1 in admixture with a biologically inert carrier.

4. A compound according to claim 2 where U, V and W are all OH, R is phosphono and R' is 4-octyloxyphenyl.

5. A compound according to claim 2 where U and W are H and V is OH, R is phosphono and R' is 4-octyloxyphenyl.

6. A method for treating mycotic infections in patients in need of therapy comprising administering a therapeutically effective amount of a compound of claim 1.

7. A method for preventing or treating *Pneumocystis carinii* infections in immune comprised patients which comprises administering a preventative or therapeutically effect amount of the compound of claim 1.

* * * * *